United States Patent [19]

Tripp et al.

[11] Patent Number: 4,614,515

[45] Date of Patent: Sep. 30, 1986

[54] DRUG DELIVERY SYSTEM

[75] Inventors: Edward S. Tripp, Grayslake; Mark E. Larkin, Lindenhurst, both of Ill.

[73] Assignee: Abbott Laboratories, North Chicago, Ill.

[21] Appl. No.: 800,369

[22] Filed: Nov. 21, 1985

Related U.S. Application Data

[63] Continuation of Ser. No. 590,601, Mar. 19, 1984, abandoned.

[51] Int. Cl.[4] .............................................. A61B 19/00

[52] U.S. Cl. ..................................... 604/403; 604/416

[58] Field of Search ............... 604/403, 404, 202, 416, 604/83, 85, 86

[56] References Cited

U.S. PATENT DOCUMENTS

| | | | |
|---|---|---|---|
| 708,264 | 9/1902 | Sherman . | |
| 2,465,269 | 3/1949 | Rohde et al. . | |
| 2,513,029 | 6/1950 | LaPointe | 604/403 |
| 2,525,958 | 10/1950 | Seager et al. . | |
| 2,746,632 | 5/1956 | Bramming . | |
| 2,969,158 | 1/1961 | Baumann | 604/404 |
| 2,977,014 | 3/1961 | Kock . | |
| 3,325,031 | 6/1967 | Singier . | |
| 3,394,831 | 7/1968 | Bathish et al. . | |
| 3,915,212 | 10/1975 | Bujan et al. . | |
| 3,946,891 | 3/1976 | Picoy et al. . | |
| 3,970,207 | 7/1976 | Faulstich . | |
| 3,976,069 | 8/1976 | Ong | 604/202 |
| 4,187,893 | 2/1980 | Bujan . | |
| 4,194,640 | 3/1980 | Crankshaw et al. | 604/416 |
| 4,244,478 | 1/1981 | Handman . | |
| 4,342,724 | 8/1982 | Narra | 604/403 |
| 4,515,586 | 5/1985 | Mendenhall et al. . | |

*Primary Examiner*—John D. Yasko

*Attorney, Agent, or Firm*—Neuman, Williams, Anderson & Olson

[57] ABSTRACT

A stoppered drug vial forms part of a drug delivery system which maintains the sterility of the drug in storage, dilution and use. A removable, pierceable diaphragm is placed over the stopper which seals the vial. The removable, pierceable diaphragm is held in place by attachment to a skirt member which encloses and is in frictional contact with the upper portion of the vial wall. Access to the drug in the vial may be obtained by either removing the diaphragm and the stopper or piercing the diaphragm and the stopper with a cannula.

48 Claims, 9 Drawing Figures

DRUG DELIVERY SYSTEM

This application is a continuation of application Ser. No. 590,601, filed Mar. 19, 1984, now abandoned.

BACKGROUND OF THE INVENTION

This invention relates to a drug delivery system which both stores and subsequently affords sterile access to the contents of a drug containing vial. More particularly, this invention relates to a drug delivery system which allows sterile access to a packaged drug, either by the utilization of a syringe or direct insertion of the drug containing vial into a fluid supply source in an I.V. administration system.

Medicaments or drugs normally administered in a health care environment, being flowable substances, are typically packaged in vials whose interior is maintained in a sterile condition. The vials themselves are sealed by a sterile stopper which is eventually pierced by a cannula when it is desired to remove the medicament or drug. Several procedures are required in order to get the drug from the vial and into the body of a patient. Each procedure is time consuming for health care personnel and more importantly each procedure presents a risk of jeopardizing the sterility of the vial, the stopper or the medicament.

If the medicament in a particular vial is a powder the procedures which may jeopardize sterility include adding diluent to the vial to dissolve the powder and then subsequently further diluting the concentrated diluent-medicament solution to the desired strength. When the medicament or drug can be administered directly to a patient, a cannula and syringe assembly may be used to make an injection through the skin of the patient or into a Y-site in an I.V. administration set. If the medicament or drug is of such a strength or potency that it must be administered over a prolonged period of time then the medicament or drug is mixed with a large quantity of diluent and placed into a container which becomes a secondary fluid source in a piggyback I.V. administration system. If there is no primary fluid source in an I.V. administration system the medicament and diluent solution may itself be administered intravenously to a patient.

The problem, therefore, experienced by health care and pharmacy personnel with prior art drug delivery systems is two-fold. First, multiple time consuming procedures are required in order to take the drug from its storage condition to a condition in which it can be properly and safely administered to a patient. Second, each procedure between storage and administration presents a new opportunity for jeopardizing drug stopper or vial sterility. The need exists, therefore, to provide a system by which the possibility of contamination of a drug, the vial and the stopper are minimized between storage and administration.

Nowhere in the art is there found a drug delivery system which minimizes the procedures between storage and administration and simultaneously assures sterility of the drug, the stopper and the vial.

U.S. Pat. No. 2,997,014 discloses enclosing a vial within a separate container for protection against damage, U.S. Pat. No. 3,394,831 discloses the addition of a tear strip to facilitate opening of a protective package surrounding a medicament container. The utilization of a U-shaped stopper to securely lock and unlock the opening in a vial is disclosed in U.S. Pat. No. 2,746,632.

Covering the stopper in the vial with a sealing disk to maintain sterility of the stopper is disclosed in U.S. Pat. No. 4,244,478, and formation of a handle or hanger at the base of a container is disclosed in U.S. Pat. No. 3,325,031 to Singier.

SUMMARY OF THE INVENTION

A system is provided for storage and delivery of a drug or medicament for health care or pharmacy personnel. The drug or medicament is sealed within a vial by a removable, pierceable stopper in the vial opening. Positioned over the stopper in the vial opening is a removable, pierceable diaphragm. Circumscribing the outside of the vial is a skirt member which is in frictional contact with the wall portion of the vial. The diaphragm is connected to the skirt member so that access to the interior of the vial may be obtained by either piercing the diaphragm and the stopper with the point of a cannula or completely separating the diaphragm from the skirt member so that the stopper may be removed from the vial opening. In the preferred embodiment the separation of the diaphragm from the skirt member is accomplished by the use of frangible sections circumscribing that portion of the skirt member which connects the portion of the skirt member in frictional contact with the wall portion of the vial and the diaphragm. Once the diaphragm has been removed from its position over the stopper, the stopper may be removed from the vial and the contents of the vial added to an intravenous administration system without compromising sterility of the drug, the vial or the stopper. A system disclosing an apparatus for making a direct addition of a medicament or drug to a flexible container for eventual use as either a primary or secondary fluid source in I.V. therapy is disclosed in application Ser. No. 565,126, filed on Dec. 23, 1983 assigned to the same assignee as the present application and is incorporated herein by reference.

BRIEF DESCRIPTION OF THE DRAWINGS

A further understanding of the drug delivery system of this invention may be had by reference to the drawings wherein.

DESCRIPTION OF THE EMBODIMENTS

Figure 1:
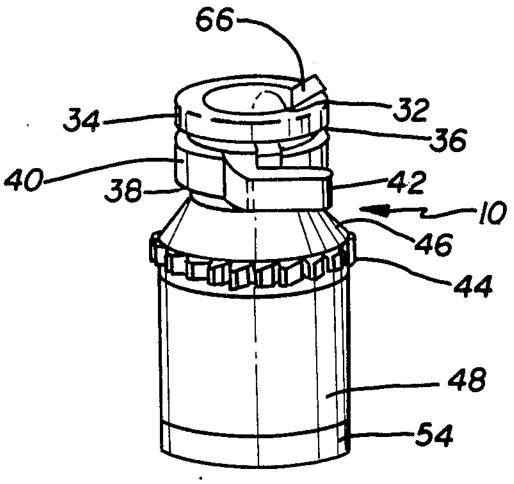
FIG. 1 is a perspective view of the drug delivery system of this invention.
Figure 3:
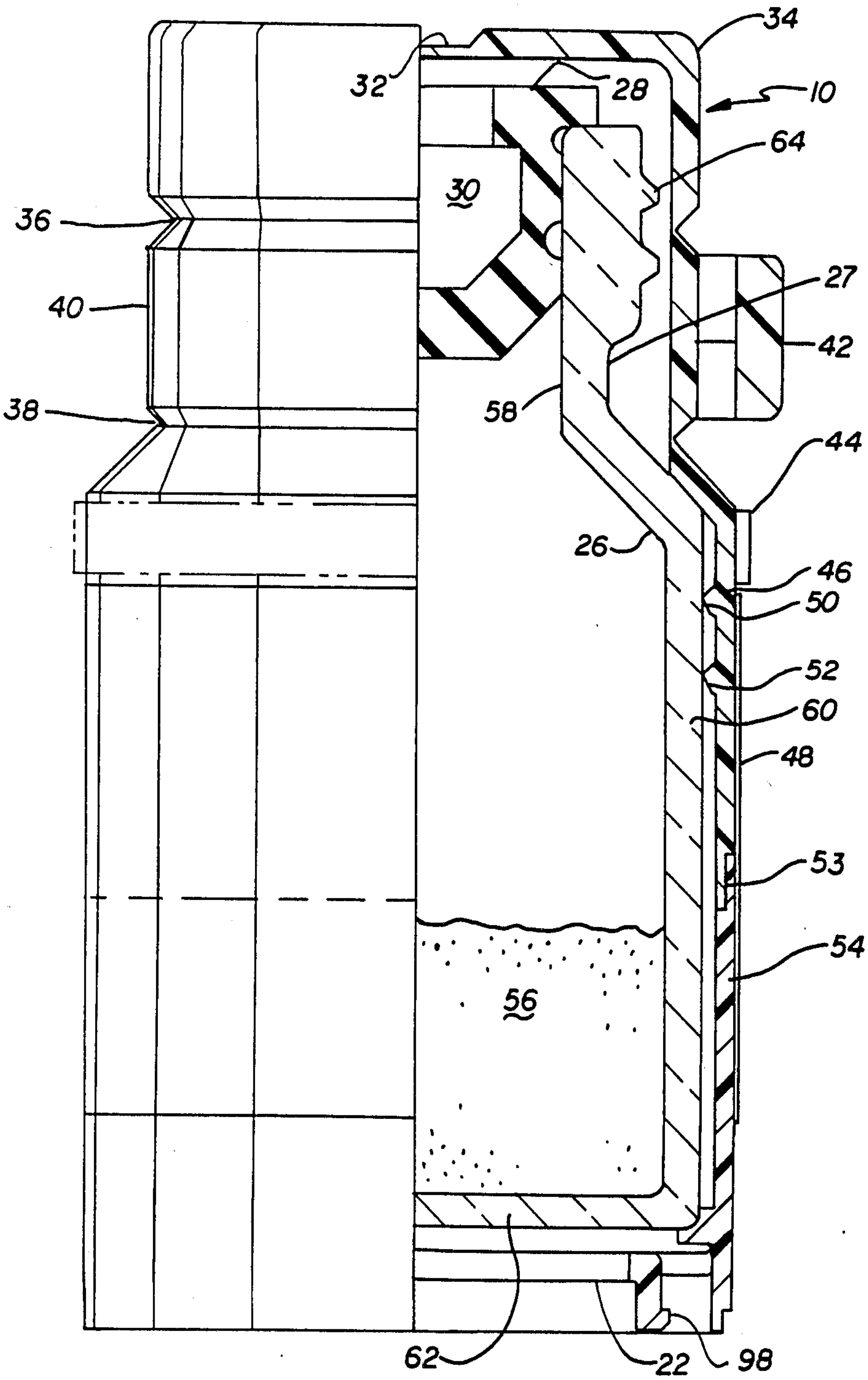
FIG. 3 is a front view in partial section of the drug delivery system illustrated in FIG. 1.
Figure 4:
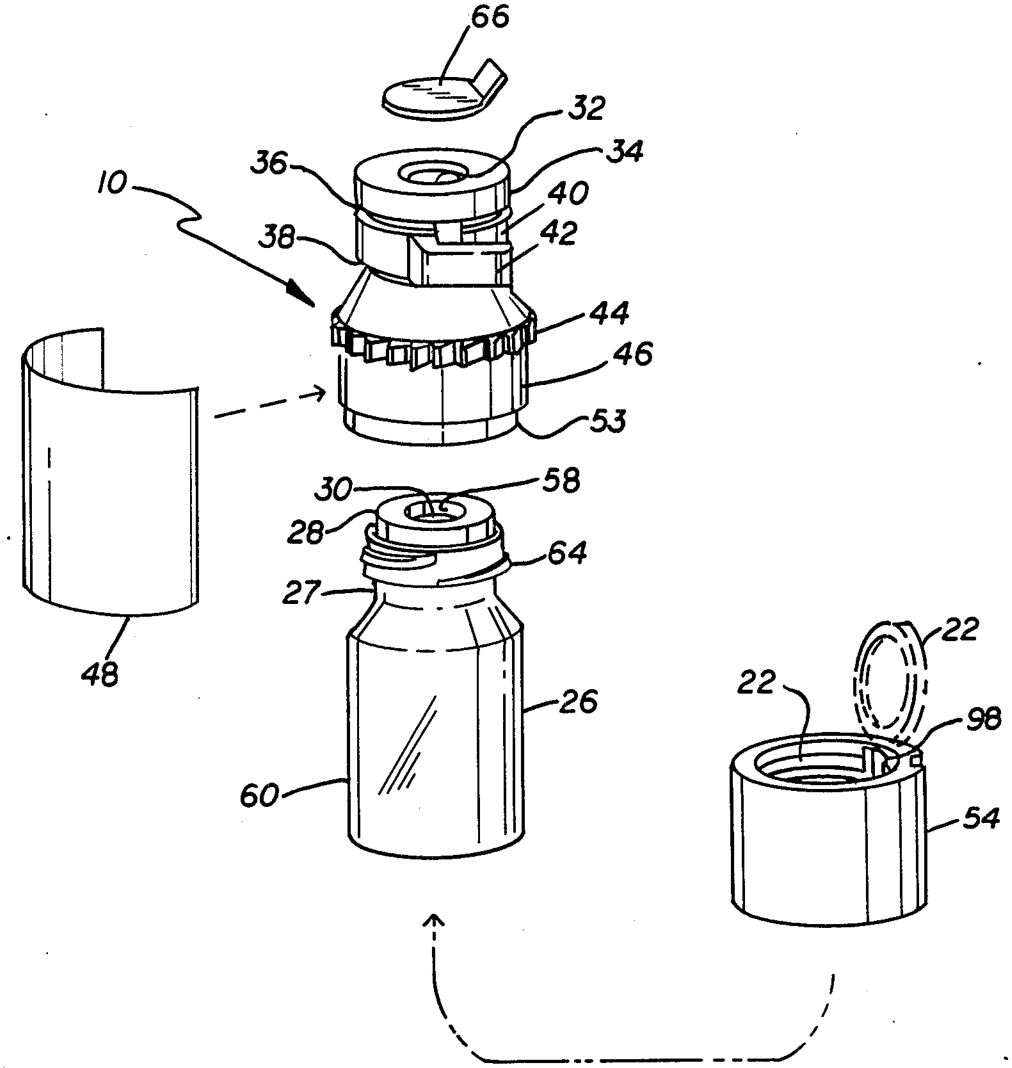
FIG. 4 is an exploded assembly view of the the drug delivery system illustrated in FIG. 1.

FIG. 1 illustrates the preferred embodiment of the drug delivery system 10 as it will be received by health care personnel or hospital pharmacies. The drug is identified to the user by label 48. Shroud member 54 and skirt member 46 form a sleeve which surrounds the drug-containing vial 26 (FIGS. 3 and 4). Integral with skirt member 46 is tear strip 40 which may be removed from system 10 by grasping tab 42. Once tear strip 40 has been removed, pierceable diaphragm 32 may also be removed so as to expose the top of vial 26. When in place, however, diaphragm 32, tear strip 40 and skirt member 46 maintain the upper portions of vial 26 and stopper 28 (FIGS. 3 and 4) in a sterile condition.

Figure 2:
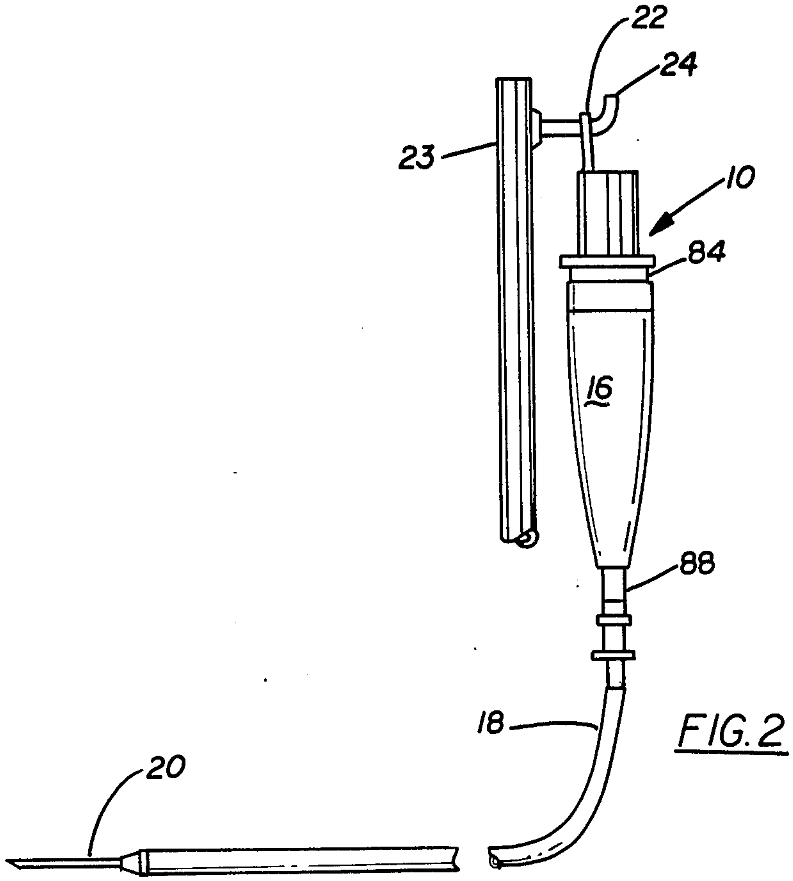
FIG. 2 is a side elevational view of the drug delivery system of this invention in conjunction with an I.V. administration system.
Figure 7:
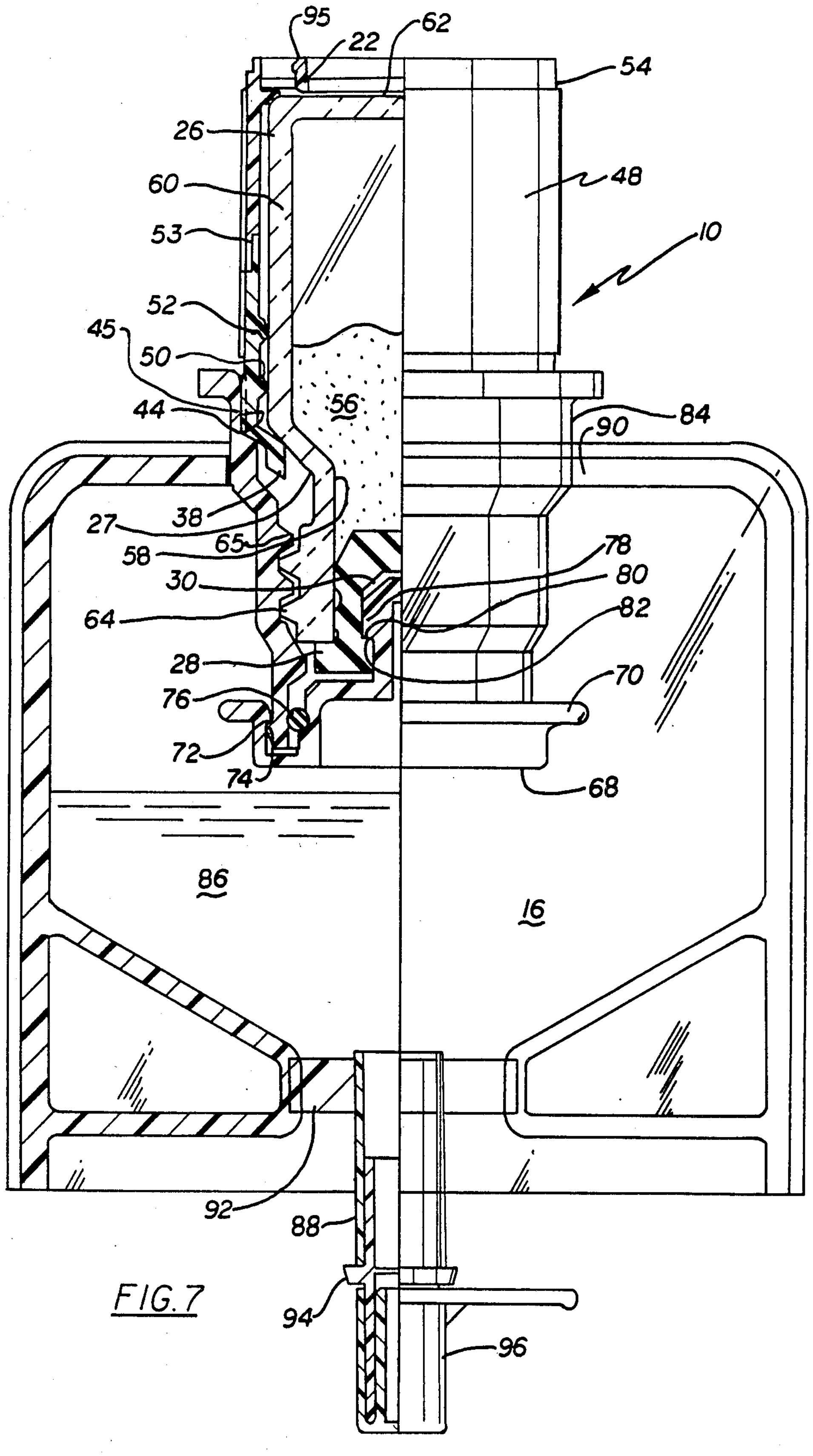
FIG. 7 is a side elevational view in partial section of the drug delivery system of the present invention inserted in a port on a flexible diluent container.

As will be explained in greater detail below, system 10 may also be used with a standard syringe 12 (FIG. 5) once peelable seal 66 has been removed. In FIG. 2, system 10 is shown forming part of a fluid source 16, typically a flexible container, which is further connected to tubing 18 and catheter or cannula 20 for intravenous administration of medicament and diluent to a patient. In this mode of operation the need to maintain the top portion of vial 26 and stopper 28 in a sterile condition can best be seen as neck 27 of vial 26 is in close proximity to the diluent in flexible container 16 (FIG. 7).

The construction of system 10 which facilitates the maintenance of sterility and ease of operation is shown more specifically in FIGS. 3 and 4. A vial 26 is used to contain a flowable substance such as a powdered or liquid medicament 56. While a circular vial 26 having a tapered neck 27 is shown it will be understood that the shape of the vial is not critical to the operation of the system of the present invention.

A removable, pierceable stopper 28 seals opening 58 of vial 26 and maintains sterility of medicament 56. Stopper 28 is shown as being substantially U-shaped in the preferred embodiment; that is having depression 30 oriented so that the bottom of the U-shape is toward the medicament 56 and the arms of the U-shape seal against opening 58. It is to be understood that any stopper design such as one including a protuberance emanating outwardly from the stopper which facilitates removal of the stopper may be used in place of the U-shaped configuration shown.

The finish or top of vial 26 is shown in the preferred embodiment with threads 64 circumscribing the outside portion of opening 58. Alternatively a nonthreaded vial 26 or vial whose finish includes an annular ring may be used.

Positioned over stopper 28 is a removable, pierceable diaphragm 32. Depending downward from the sides of pierceable diaphragm 32 is connection section 34. Connection section 34 terminates at frangible section 36 which circumscribes connection section 34. While a frangible section 36 is shown in connection with the preferred embodiment its presence is not critical to the operability of the invention. Alternatively any type of weakened section may be used. If desired, a second frangible section 38 may be used to form tear strip 40 which circumscribes the connection section 34 and the neck 27 of vial 26.

Further depending from tear strip 40 along the wall portion 60 of vial 26 is skirt member 46 which like connection section 34 circumscribes vial 26. On the inside of skirt member 46 are found rib members 50 and 52 which are in frictional engagement with wall portion 60 of vial 26. While rib member 50 and 52 are shown in connection with the preferred embodiment of the system 10 their presence is not critical to the operability of the invention. Alternatively, skirt member 46 may be in direct contact with either neck 27 or wall portion 60 of vial 26. In the preferred embodient rib members 50 and 52 form a barrier to maintain neck 27, threads 64 and stopper 28 in a sterile condition. Therefore, pierceable diaphragm 32 is held in position over stopper 28 by being integral with connection section 34 which is in turn integral with skirt member 46 which is in frictional engagement with wall portion 60 of vial 26.

The outer surface of pierceable diaphragm 32 is protected and maintained in a sterile condition by peelable adhesive seal 66. Circumscribing skirt member 46 is a ring of ratchet teeth 44 which prevents removal of system 10 from a fluid source 16 (FIGS. 2 and 7). While ratchet teeth 44 are shown in connection with the preferred embodiment, their presence is not critical to the operability of the invention.

The bottom 62 and lower section of wall portion 60 of vial 26 are protected by shroud member 54 which is constructed to mechanically engage skirt member 46. While shroud member 54 is shown in conjunction with the preferred embodiment of system 10 its presence is not critical to the operability of the invention. Additionally, while stepped engagement 53 is shown between shroud member 54 and skirt member 46 any suitable method of fitting skirt member 46 and shroud member 54 together, such as a tongue and groove, may be used. Shroud member 54 has an integral swing-up hanger portion 22 which may be utilized to hang the system 10, such as shown in FIG. 2. While hanger 22 is shown as a ring, any suitable design may be employed. Latch hook 98 may be added to hanger 22 in order to facilitate the hanging of system 10 as shown in FIG. 2. Latch hook 98 engages the bottom of shroud member 54 when hanger 22 is swung away from bottom 62 of vial 26 as shown in phantom in FIG. 4.

Label 48 may be utilized to maintain shroud member 54 in mechanical engagement 53 with skirt member 46 by placing that side of label 48 having adhesive in contact with skirt member 46 and shroud member 54. Alternatively frictional fitment such as threadable engagement or adhesive at engagement 53 may be used to maintain shroud member 54 in contact with skirt member 46.

Figure 9:
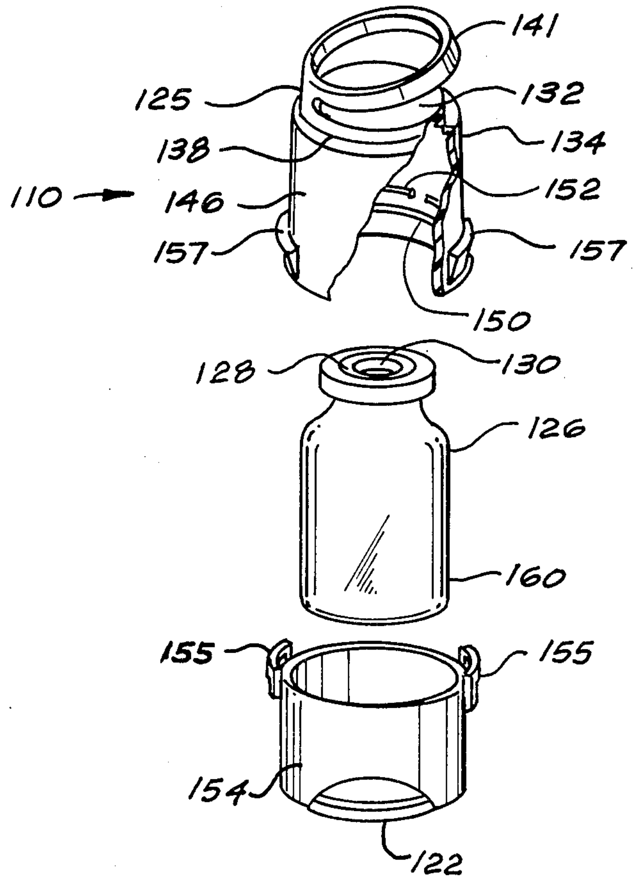
FIG. 9 is an exploded assembly view of an alternate embodiment of the drug delivery system of the present invention.

In alternate embodiment 110 of the drug delivery system of the present invention, as shown in FIG. 9, reference numbers in the "100" series have been used to designate those portions having similar construction, function and location to the parts of the preferred embodiment.

In the alternate embodiment 110, a pull ring 141 is used to apply mechanical force for the separation of pierceable diaphragm 132 from connection section 134 along tear detail 138. Hook means 155 engage ledges 157 on skirt member 146 to hold shroud member 154 in mechanical engagement with skirt member 146 and also in position over wall portion 160 of vial 126. As illustrated by rib member 152, the barrier rib members may be interrupted in a known manner.

OPERATION

Figure 5:
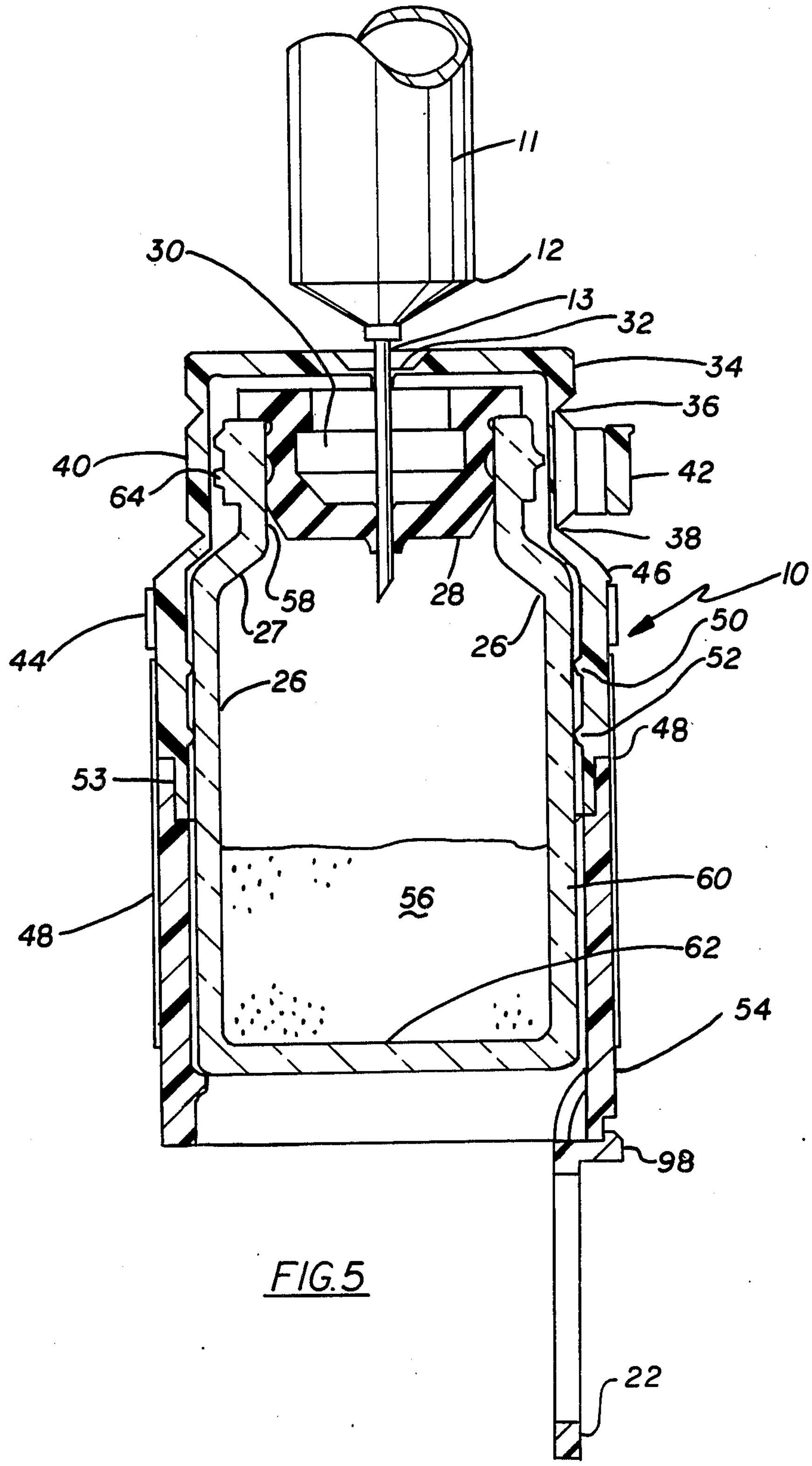
FIG. 5 is a sectional view of the drug delivery system of the present invention in use with a syringe.

Utilization of system 10 with a syringe 12 is shown in FIG. 5. This is accomplished by removing peelable adhesive seal 66 (FIG. 4) and inserting cannula 13 through pierceable diaphragm 32. Once having passed through pierceable diaphragm 32, cannula 13 will then pass through depression 30 in stopper 28 before passing through the bottom portion of stopper 28 and entering the interior of vial 26 which contains medicament 56. If medicament 56 is a powder, diluent contained in barrel 11 of syringe 12 may be added through cannula 13 to the interior of vial 26, thereby allowing extraction of medicament 56 into barrel 11 of syringe 12 once medicament 56 has been dissolved in the diluent. If medicament 56 is in liquid form, it may be drawn directly from the interior of vial 26 into the barrel 11 of syringe 12.

Figure 6:
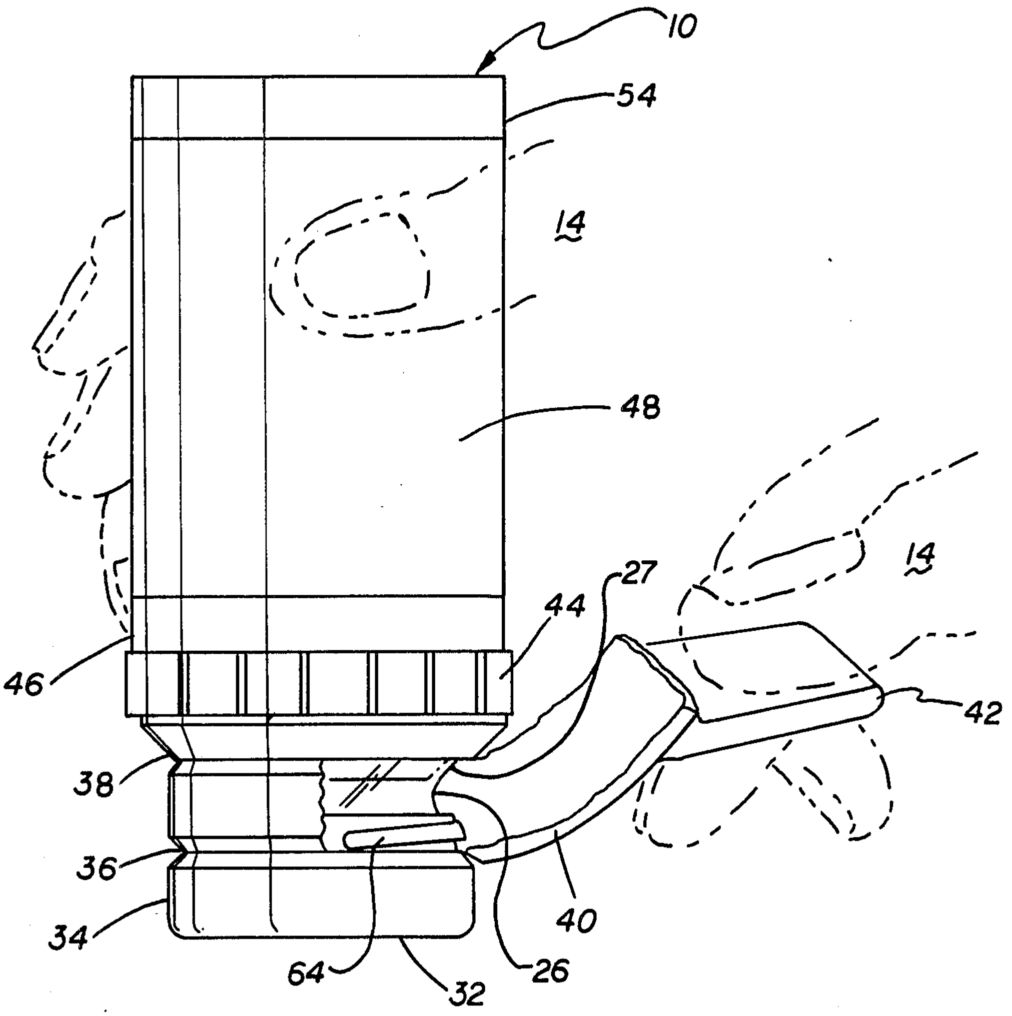
FIG. 6 is a perspective view of the drug delivery system of the present invention illustrating removal of the tear cap.
Figure 8:
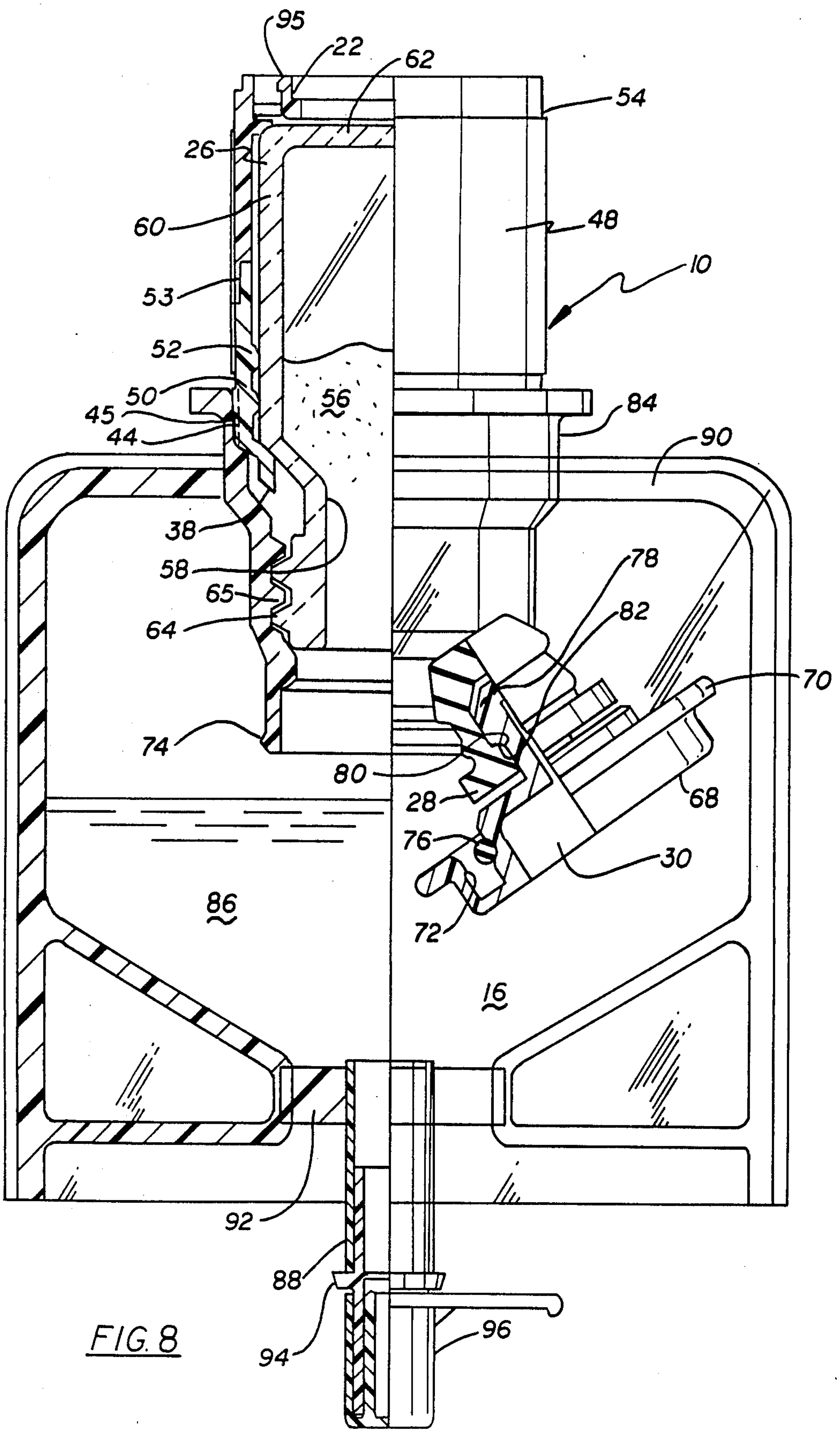
FIG. 8 is a side elevational view in partial section of the drug delivery system of the present invention in fluid communication with the diluent in a flexible diluent container.

In the preferred mode of operation of system 10, as shown in FIGS. 6, 7 and 8, tab member 42 which is formed as part of tear strip 40 is grasped by fingers 14 and pulled away from skirt member 46. This pulling action will cause tear strip 40 to peel away from neck 27 of vial 26, by severing itself from connecting portion 34 and skirt member 46 at frangible sections 36 and 38. Once tear strip 40 has been completely removed from skirt member 46 and connection section 34, nothing remains to retain pierceable diaphragm 32 in its position over stopper 28 and it will therefore may be removed from system 10.

As shown in FIG. 7 neck 27 of vial 26 may now be inserted into port or sleeve 84 in fluid source 16 which is typically a flexible bag partially filled with diluent. This interengagement of vial 26 and sleeve 84 is accomplished by threadable engagement of threads 64 with complementary threads 65 within sleeve 84. Rotating vial 26 with respect to fluid source 16 causes neck 27 to be drawn into sleeve 84. This drawing action causes protuberance 78 from cover 68 on sleeve 84 to enter depression 30 in stopper 28. When protuberance 78 has completely entered depression 30 lip 80 of protuberance 78 will be in a position over ledge 82 in stopper 28. Ratchet teeth 44 engage compatible ratchet teeth 45 in sleeve 84. The slopes of compatible ratchet teeth 44 and 45 are such that system 10 cannot be backed out of sleeve 84 once interengagement has begun. Cover 68 is in sealing engagement with the bottom of sleeve 84 by the compression of O-ring 76 and by mechanical engagement of lip 72 over ledge 74 on the bottom of sleeve 84.

Once system 10 is in place in fluid source 16, medicament 56 may be mixed with diluent 86 as shown in FIG. 8. By using the flexible properties of liquid source 16 the user may grasp flange 70 of cover 68. In doing so, the user may then manipulate cover 68 so that lip 72 rides over ledge 74, thus removing cover 68 from its mechanical engagement with the bottom of sleeve 84. As cover 68 is removed from the sleeve 84, the mechanical engagement of lip 80 on protuberance 78 against ledge 82 on stopper 28 will cause stopper 28 to be removed along with cover 68. This manipulation of cover 68-stopper 28 combination will create an open path through vial opening 58 for medicament 56 to intermix with diluent 86. Diluent 86 and medicament 56 may be further intermixed by squeezing the sides of liquid source 16. Hanger 22 may then be swung up and away from bottom 62 of vial 26 and used to hang the fluid source from a hook 24 on an I.V. pole 23 as shown in FIG. 2. Hanger 22 is retained in position by the action of latch hook 98 at the base of hanger 22 which engages the bottom portion of shroud member 54. Tubing 18 and catheter or cannula 20 (FIG. 2) are placed in fluid communication with the interior of fluid source 16 once cap 96 has been removed from port insert 94.

Should it be desired to administer two drugs simultaneously, a second drug may be added to vial 26 by use of syringe 12 before tear strip 40 is removed to utilize system 10 with fluid source 16. In the situation where a custom blend of medication is required, empty vials may be supplied and then later filled with the custom blend of medication for temporary storage before later use with a fluid source or a flexible fluid storage container.

Alternative embodiment 10 is operated in essentially the same manner as preferred embodiment 10; however pierceable diaphraghm 132 is separated from skirt member 146 by means of a pull ring 141 rather than a tear strip 40 (FIG. 6). Additionally vial 126 is shown with an unthreaded finish when utilization without threadable engagement such as a snap or frictional fitment is desired.

Systems 10 and 110 are made in substantially the same manner. Medicament 56 is first inserted into vial 26. Stopper 28 is then placed in opening 58 of vial 26. Skirt member 46 is then placed over vial 26 so that pierceble diaphragm 32 is positioned over stopper 28 and seal rings 50 and 52 are in frictional engagement with wall portion 60 of vial 26. Once in proper position, tear strip 40 will circumscribe neck 27 of vial 26. Shroud member 54 is then placed over the bottom of wall portion 60 and further moved to mechanically engage 53 skirt member 46. Label 48 is then wrapped around skirt member 46 and shroud member 54 so that skirt member 46 and shroud member 54 are maintained in close proximity.

Referring specifically to FIGS. 7 and 8, sleeve 84 is typically mandrel sealed 90 into the edge of liquid source 16 as is administration port 88 mandrel sealed 92 into another portion of liquid source or flexible container 16. Skirt member 46, tear strip 40, connecting portion 34, and pierceable diaphragm 32 of system 10 are typically made of a polypropylene plastic, as is shroud member 54. Alternatively, other suitable medical grade plastics such as polyvinyl chloride or polyethylene may be used. Vial 26 is constructed of glass; however it may also be constructed from polyethylene, polypropylene or any suitable medical grade barrier plastic or plastic combination. Stopper 28 is typically made of rubber; however, other suitable flexible medical grade plastics such as a styrene butadiene copolymer may be used in the place of rubber. Peelable adhesive seal 66 and label 48 are fabricated from paper or foil which has been coated with an adhesive compatible with the materials from which drug delivery system 10 has been fabricated. It should be further understood that the term "flowable" as employed in the specification and claims is meant to imply any material which will flow from one container to another whether liquid, solid or gas.

It will thus be seen that through the present invention there is now afforded a drug delivery system in which the procedures between storage and administration of a drug are minimized. Activation of the drug delivery system by health care or pharmacy personnel may be readily accomplished without the use of specially designed components or sophisticated methods which require an excessive number of procedures or prolonged exposure which might jeopardize sterility.

The foregoing invention can now be practiced by those skilled in the art. Such skilled persons will know that the drug delivery system of the present invention is not necessarily restricted to the particular embodiments presented herein. The scope of the present invention is to be defined by the terms of the following claims as given meaning by the preceding description.

We claim:

1. A storage and delivery system for delivering a flowable substance into a container provided with stopper removal means, comprising:

a vial having an opening, a wall portion and a bottom constructed and arranged to contain the flowable substance;

a removable, pierceable stopper in sealing engagement with said opening in said vial, said stopper including means for engagement with such a stopper removal means for removal of said stopper from said vial by said removal means;

a removable, pierceable diaphragm positioned over said stopper whereby the flowable substance may be extracted from said vial through a cannula inserted into said vial through said diaphragm and said stopper;

a skirt member in engagement with said wall portion of said vial; and means for detachably attaching said removable, pierceable diaphragm to said skirt member to retain said diaphragm over said stopper and to permit detachment and removal of said diaphragm to expose said stopper so that the stopper may be engaged with a stopper removal means.

2. The system as defined in claim 1 wherein said vial opening, said removable, pierceable stopper and said wall portion of said vial enclosed by said means for attaching said removable, pierceable diaphragm to said skirt member are maintained in a sterile condition.

3. The system as defined in claim 1 wherein said means for attaching said removable, pierceable diaphragm to said skirt member is circumscribed by at least one frangible section.

4. The system as defined in claim 1 wherein said removable, pierceable diaphragm is maintained in a sterile condition by being covered with a peelable adhesive seal.

5. The system as defined in claim 1 wherein frictional engagement of said skirt member with said wall portion of said vial is provided by at least one rib member.

6. The system as defined by claim 1 further including a shroud member enclosing that portion of said wall portion of said vial not enclosed by said skirt member.

7. The system as defined in claim 6 wherein said shroud member and said skirt member are in mechanical engagement.

8. The system as defined in claim 7 wherein said mechanical engagement is a frictional engagement.

9. A medicament storage and delivery system comprising:

a vial having an opening, a wall portion and a bottom;

a removable, pierceable stopper in sealing engagement with said opening in said vial;

a removable, pierceable diaphragm positioned over said stopper;

a skirt member in frictional engagement with said wall portion of said vial;

a connection section circumscribed by a frangible portion constructed and arranged to attach said removable, pierceable diaphragm to said skirt member;

a shroud member covering that section of said wall portion of said vial not covered by said skirt member; and means for hanging said medicament storage and delivery system formed as a part of said shroud member.

10. The medicament storage and delivery system as defined in claim 9 in combination with a flexible fluid container having a port, wherein said skirt member and said port in said flexible fluid container have complementary ratchet teeth.

11. The system as defined in claim 9 wherein said stopper has a depression constructed and arranged to be engagable with means to remove said stopper from said vial.

12. The system as defined in claim 9 for use with a fluid storage container having a port and vial engagement means, said vial having complementary engagement means whereby fluid communication between the interior of said vial and the interior of the fluid storage container is accomplished by interengagement of said vial with said port in said fluid container.

13. The system as defined in claim 9 for use with a fluid container having a port and threadable means for engaging a vial in association with said port, said vial having complementary threadable means whereby interengagement of said opening in said vial with said port in said fluid container is accomplished by said complementary threadable means.

14. The system as defined in claim 1, 2, 3, 7 or 8 wherein said skirt member is in frictional engagement with said wall portion of said vial.

15. The system as defined in claim 1, or 9 in combination with a fluid container having a port and means for engaging a vial in association with said port, said vial having complementary engagement means whereby interengagement of said opening in said vial with said port in said fluid container is accomplished by relative rotational engagement between said engaging means and said complementary engagement means, and complementary ratchet means on said port and on said vial for interengagement upon such rotational engagement of said engaging means and said complementary engagement means to thereafter prevent disengagement of said vial from said fluid container.

16. The combination as in claim 15 wherein said engaging means and said complementary engagement means are complementary threads on said port and on said vial.

17. The combination as in claim 16 wherein said complementary ratchet means are ratchet teeth on said port and said vial.

18. The combination as in claim 15 wherein said ratchet means on said vial are ratchet protuberances on said skirt member.

19. The combination as in claim 15 including means for removing said removable stopper after said vial is interengaged with said port.

20. A storage and delivery system for delivering a flowable substance, comprising:

a vial having an opening, a wall portion and a bottom constructed and arranged to contain the flowable substance;

a removable, pierceable stopper in sealing engagement with said opening in said vial, said stopper including means for engagement for removal of said stopper from said vial;

a removable, pierceable diaphragm positioned over said stopper whereby the flowable substance may be extracted from said vial through a cannula inserted into said vial through said diaphragm and said stopper;

a skirt member in engagement with said wall portion of said vial; and means for detachably attaching said removable, pierceable diaphragm to said skirt member to retain said diaphragm over said stopper and to permit detachment and removal of said diaphragm to expose said stopper so that the stopper may be engaged for removal from said vial.

21. A storage and delivery system for a flowable substance comprising:

a vial having an opening, a wall portion and a bottom constructed and arranged to contain the flowable substance;

a removable, pierceable stopper in sealing engagement with said opening in said vial;

a removable, pierceable diaphragm positioned over said stopper;

a skirt member in frictional engagement with said wall portion of said vial; and means for attaching said removable, pierceable diaphragm to said skirt member, said means for attaching said removable, pierceable diaphragm to said skirt member being circumscribed by two frangible sections and further having a tab member located therebetween.

22. A storage and delivery system for a flowable substance comprising:

a vial having an opening, a wall portion and a bottom constructed and arranged to contain the flowable substance;

a removable, pierceable stopper in sealing engagement with said opening in said vial;

a removable, pierceable diaphragm positioned over said stopper;

a skirt member in frictional engagement with said wall portion of said vial;

means for attaching said removable, pierceable diaphragm to said skirt member;

a shroud member enclosing that portion of said wall portion of said vial not enclosed by said skirt member; and said shroud member and said skirt member being secured together by the use of a label having adhesive on one side, wherein said adhesive is in contact with said shroud and said skirt members.

23. A storage and delivery system for delivering a flowable substance into a fluid container having a port, first means for rotatively engaging a vial in communication with said port and ratchet means associated with said port, said system comprising:

a vial having an opening, a wall portion and a bottom constructed and arranged to contain such a flowable substance;

complementary engagement means on said vial for affixing said vial to such a fluid container, with said opening in communication with said port, by relative rotational engagement between said complementary engagement means and such engaging means;

complementary ratchet means on said vial for interengagement with said port ratchet means upon such rotational engagement of said engaging means and said complementary engagement means to thereafter prevent disengagement of said vial from said fluid container; and a removable barrier member in sealing engagement with said opening in said vial and adapted for removal therefrom subsequent to such engagement of said vial with such a fluid container.

24. The invention as defined in claim 23 wherein said barrier member includes means for engagement with barrier removing means of such a fluid container upon such engagement of said vial with fluid container.

25. The invention as defined in claim 23 wherein said removable barrier member is a stopper in said vial opening, said stopper having means for engagement with stopper removing means of such a fluid container upon such engagement of said vial with said fluid container.

26. The invention as in claim 23 including a cover over said opening and said removable barrier member for maintaining said opening and said removable barrier in a sterile condition, and means for detachably attaching said cover to said wall portion to permit detachment and removal of said cover to expose said opening and said barrier member for attachment of said vial to such a port.

27. A storage and delivery system for delivering a flowable substance into a fluid container having a port, first means for rotatively engaging a vial in communication with said port, ratchet means associated with said port and means for removing a stopper from the opening of such a vial in communication with said port, comprising:

a vial having an opening, a wall portion and a bottom constructed and arranged to contain such a flowable substance;

a removable stopper in sealing engagement with said opening in said vial, said stopper including means for engagement with such a stopper removal means of such a fluid container, when said vial is engaged with said fluid container, for subsequent removal of said stopper from said vial by said removal means;

a removable cover positioned over said stopper;

a skirt member in engagement with said wall portion of said vial;

means for detachably attaching said removable cover to said skirt member to retain said cover over said stopper and to permit detachment and removal of said cover to expose said stopper so that the stopper may be engaged with a stopper removal means, and complementary ratchet means on said vial for interengagement with said port ratchet means upon such rotational engagement of said engaging means and said complementary engagement means to thereafter prevent disengagement of said vial from said fluid container.

28. The invention as in claim 27 wherein said ratchet means on said vial are ratchet protuberances on said skirt member.

29. A medicament storage and delivery system comprising:

a fluid container having a port;

a vial having an opening, a wall portion and a bottom constructed and arranged to contain a flowable substance;

a removable barrier member in sealing engagement with said opening in said vial;

said vial and said port having complementary engagement means affixing said vial to said fluid container with said opening in said vial in communication with said port by relative rotational movement between said vial and fluid container;

complementary interengaging ratchet means on said port and on said vial for effecting said interengagement upon such relative rotational engagement movement of said vial and said fluid container and preventing disengagement of said vial from said fluid container; and means for removing said barrier member from the opening of said vial with said opening in communication with said port.

30. The invention as defined in claim 29 wherein said removable barrier is a stopper in said vial.

31. The invention as defined in claim 29 wherein said removing means comprises an element affixed to said container and said barrier member comprises a stopper in said vial and engaging said removing means.

32. The invention as in claim 29 including a cover over said opening and said removable barrier member for maintaining said opening and said removable barrier in a sterile condition, and means for detachably attaching said cover to said wall portion to permit detachment and removal of said cover to expose said opening and said barrier member for attachment of said vial to such a port.

33. The invention as in claim 23 or 29 including a cover over said opening, said removable barrier member and said complementary engagement means; and means for detachably attaching said cover to said wall portion to permit detachment and removal of said cover to expose said opening, said barrier member and said complementary engagement means for attachment of said vial to such a port.

34. The invention as in claim 23, 24, 25, 26, 27, 28, 29, 30, 31 or 32 wherein said complementary engagement means are screw threads adjacent said opening.

35. The invention as defined in claim 34 wherein said ratchet means are ratchet teeth on said port and said vial.

36. A storage and delivery system for delivering a flowable substance into a fluid container having a port, means for rotatively engaging a vial in communication with said port, ratchet means associated with said port and means for removing a barrier member from the opening of a vial in communication with said port, said system comprising:

a vial having an opening, a wall portion and a bottom constructed and arranged to contain such a flowable substance;

a removable barrier member in sealing engagement with said opening in said vial, said barrier member including means for engagement with such a removing means for removal of said barrier member from said vial by said removing means;

complementary engagement means on said wall portion adjacent said opening for rotative interengagement of said vial with such a fluid container;

a covering member including a first portion encompassing said vial opening and removable barrier member, for maintaining said opening and barrier member in a sterile condition, and a second portion engaging said wall portion for retention on said wall portion, and means for selectively detaching said first portion of said covering member for removal to expose said opening and removable barrier member for engagement with such a fluid container; and complementary ratchet means on said second portion of said covering member for interengagement with said port ratchet means of such a fluid container upon such rotational engagement of said engaging means thereof and said complementary engagement means of said vial to thereafter prevent disengagement of said vial from said fluid container.

37. The invention as defined in claim 36 and including a shroud member covering that section of said wall portion of said vial not covered by said covering member.

38. A storage and delivery system for delivering a flowable substance into a fluid container having a port and means for engaging a vial in communication with said port, said system comprising:

a vial having an opening, a wall portion and a bottom constructed and arranged to contain such a flowable substance;

a removable barrier member in sealing engagement with said opening in said vial;

complementary engagement means on said wall portion adjacent said opening for rotative interengagement of said vial with such a fluid container;

a covering member including a first portion encompassing said vial opening and removable barrier member, for maintaining said opening and barrier member in a sterile condition, and a second portion engaging said wall portion for retention on said wall portion, and means for selectively detaching said first portion of said covering member for removal to expose said opening and removable barrier member for engagement with such a fluid container;

a shroud member covering that section of said wall portion of said vial not covered by said skirt member; and means for hanging said storage and delivery system formed as a part of said shroud member.

39. The invention as defined in claim 36, 37 or 38 including a hanger adjacent said bottom of said vial and attached to said shroud.

40. The invention as defined in claim 39 wherein said hanger includes means to retain said hanger in an outwardly disposed position relative to said vial for facilitating the hanging of said system.

41. The invention as defined in claim 36, 37 or 38 wherein said second portion of said covering member is in frictional engagement with said wall portion of said vial.

42. The invention as defined in claim 37 or 38 wherein said shroud and said second portion of said covering member are in mechanical engagement with one another over said wall portion of said vial.

43. The invention as defined in claim 37 or 38 including a label adhesively attached to said shroud member and said second portion of said covering member for securing said members together.

44. The invention as defined in claim 36, 37 or 38 wherein said first portion of said covering member includes a pierceable diaphragm and said removable barrier member is a pierceable stopper.

45. The invention as defined in claim 44 and including a peelable seal adhesively attached to said first portion of said covering member over said diaphragm for maintaining said diaphragm in a sterile condition.

46. The invention as defined in claim 36, 37 or 38 wherein said selective detaching means includes a frangible section, and a pull tab integral with said covering member for gripping by the user to detach said first portion.

47. The invention as defined in claim 46 wherein said pull tab is ring shaped.

48. The invention as defined in claim 46 wherein said selective detaching means comprises two spaced frangible sections circumscribing said covering member, and said pull tab is integral with the portion of said covering member between said frangible sections.

* * * * *

UNITED STATES PATENT AND TRADEMARK OFFICE

CERTIFICATE OF CORRECTION

PATENT NO. : 4,614,515

DATED : September 30, 1986

INVENTOR(S) : Edward S. Tripp and Mark E. Larkin

It is certified that error appears in the above-identified patent and that said Letters Patent are hereby corrected as shown below:

Col. 5, l. 22, delete "will". Col. 6, l. 10, "10" should read --110--. Col. 6, l. 21, correct the spelling of "pierceable". Col. 7, claims 2, 4, 5 and 6, correct the dependency of each of these claims to read "1, 20, 21, or 22". Col. 7, claim 3, correct the dependency of the claim 3 to read "1, 20 or 22". Col. 8, claim 14, correct the dependency of claim 14 to read "1, 2, 3, 4, 6, 7, 8 or 20". Col. 8, Claim 15, correct the dependency of claim 15 to read "1, 9 or 20".

Signed and Sealed this

Tenth Day of February, 1987

*Attest:*

DONALD J. QUIGG

*Attesting Officer*

*Commissioner of Patents and Trademarks*